(12) United States Patent
Ritz

(10) Patent No.: US 9,056,963 B2
(45) Date of Patent: Jun. 16, 2015

(54) LOW RESIDUAL BISPHENOL A ALKOXYLATED MATERIALS, THEIR PREPARATION AND USE THEREOF

(71) Applicant: Milliken & Company, Spartanburg, SC (US)

(72) Inventor: Ricky Lee Ritz, Inman, SC (US)

(73) Assignee: MILLIKEN & COMPANY, Spartanburg, SC (US)

( * ) Notice: Subject to any disclaimer, the term of this patent is extended or adjusted under 35 U.S.C. 154(b) by 0 days.

(21) Appl. No.: 14/594,271

(22) Filed: Jan. 12, 2015

(65) Prior Publication Data

US 2015/0122150 A1 May 7, 2015

Related U.S. Application Data

(62) Division of application No. 13/684,663, filed on Nov. 26, 2012.

(60) Provisional application No. 61/567,221, filed on Dec. 6, 2011.

(51) Int. Cl.
| | |
|---|---|
| C07C 43/20 | (2006.01) |
| C07C 43/23 | (2006.01) |
| C07C 37/14 | (2006.01) |
| C08K 5/13 | (2006.01) |
| C07C 41/03 | (2006.01) |
| C09D 7/00 | (2006.01) |

(52) U.S. Cl.
CPC . *C08K 5/13* (2013.01); *C07C 43/23* (2013.01); *C07C 37/14* (2013.01); *C07C 43/20* (2013.01); *C09D 7/001* (2013.01); *C07C 41/03* (2013.01)

(58) Field of Classification Search
None
See application file for complete search history.

(56) References Cited

U.S. PATENT DOCUMENTS

| | | | | | |
|---|---|---|---|---|---|
| 3,890,448 | A | * | 6/1975 | Ito | 426/126 |
| 4,866,134 | A | * | 9/1989 | Takano et al. | 525/109 |
| 5,270,368 | A | * | 12/1993 | Lent et al. | 524/236 |
| 6,342,641 | B1 | * | 1/2002 | VanDahm et al. | 568/609 |
| 6,624,333 | B1 | * | 9/2003 | Koser et al. | 568/609 |
| 8,105,679 | B2 | * | 1/2012 | Jonai et al. | 428/195.1 |
| 2004/0181099 | A1 | * | 9/2004 | Hirano et al. | 568/662 |
| 2008/0038570 | A1 | * | 2/2008 | Satou et al. | 428/483 |
| 2010/0009279 | A1 | * | 1/2010 | Hidaka et al. | 430/108.23 |
| 2010/0068644 | A1 | * | 3/2010 | Nakajima et al. | 430/109.4 |

* cited by examiner

*Primary Examiner* — Joseph D Anthony
(74) *Attorney, Agent, or Firm* — Brenda D. Wentz

(57) ABSTRACT

This invention relates to alkoxylated Bisphenol A compositions containing low residual amounts of Bisphenol A. The present invention also relates to methods for making such alkoxylated compositions containing low residual amounts of Bisphenol A, as well as uses for such compositions. The alkoxylated compositions containing low residual amounts of Bisphenol A may be utilized in packaging applications (such as indirect and/or direct food contact packaging), printing inks, container linings, and the like.

6 Claims, No Drawings

LOW RESIDUAL BISPHENOL A ALKOXYLATED MATERIALS, THEIR PREPARATION AND USE THEREOF

CROSS REFERENCE TO RELATED APPLICATIONS

This application claims priority to and is a divisional of U.S. patent application Ser. No. 13/684,663, entitled "Low Residual Bisphenol A Alkoxylated Materials, Their Preparation and Use Thereof," which was filed on Nov. 26, 2012, which claims priority to and is a non-provisional of U.S. Provisional Patent Application No. 61/567,221, entitled "Low Residual Bisphenol A Alkoxylated Materials, Their Preparation and Use Thereof" which was filed on Dec. 6, 2011, all of which are entirely incorporated by reference herein.

FIELD OF THE INVENTION

This invention relates to alkoxylated Bisphenol A compositions containing low residual amounts of Bisphenol A. The present invention also relates to methods for making such alkoxylated compositions containing low residual amounts of Bisphenol A, as well as uses for such compositions. The alkoxylated compositions containing low residual amounts of Bisphenol A may be utilized in packaging applications (such as indirect and/or direct food contact packaging), printing inks, container linings, and the like.

BACKGROUND OF THE INVENTION

Bisphenol compounds, including alkoxylated bisphenols, are used as raw materials in many chemical compositions. They are useful as monomers for epoxy, polyester and polyurethane resins and reactive diluents in high solids coatings. These materials are typically made by combining a bisphenol compound with an alkylene oxide compound in the presence of a base catalyst under elevated temperature and pressure. The resulting alkoxylated bisphenol composition contains a certain amount of bisphenol that has not reacted with the alkylene oxide compound. There is a growing demand in the marketplace for materials with low bisphenol content. More specifically, there is an increasing need for materials with low residual Bisphenol A content.

This invention provides a solution to the problem of creating materials that contain low amounts of residual Bisphenol A, and more specifically, of creating alkoxylated materials that contain low amounts of residual Bisphenol A. By modifying certain steps of the manufacturing process, the inventor has discovered that alkoxylated materials having a Bisphenol A content of less than or equal to 200 ppm can be consistently achieved. This is desirable for end use products, such as direct and/or indirect food contact packaging products, wherein the free Bisphenol A content is significantly reduced.

SUMMARY OF THE INVENTION

This invention relates to alkoxylated bisphenol compositions containing low residual amounts of Bisphenol A. The present invention also relates to methods for making such alkoxylated compositions containing low residual amounts of Bisphenol A, as well as uses for such compositions. The alkoxylated compositions containing low residual amounts of Bisphenol A may be utilized in packaging applications (such as indirect and/or direct food contact packaging), printing inks, container linings, and the like.

In one aspect, this invention relates to a composition comprising: (a) an alkoxylated Bisphenol A compound represented by structure (I):

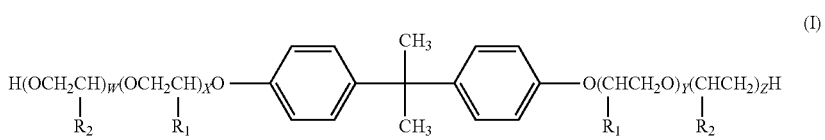

wherein $R_1$ and $R_2$ are independently selected from H, $CH_3$, $CH_2CH_3$ and wherein $x+y=2.2$ to 50 and $w+z=0$ to 50; and (b) residual Bisphenol A in an amount greater than zero but less than 200 ppm.

In another aspect, this invention relates to a composition comprising: (a) an ethoxylated Bisphenol A compound represented by structure (I):

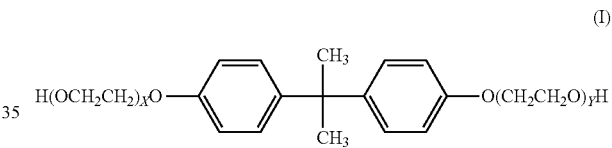

wherein $x+y=2.2$ to 50; and (b) residual Bisphenol A in an amount greater than zero but less than 200 ppm.

In a further aspect, this invention relates to a method for preparing an alkoxylated Bisphenol A composition containing low residual Bisphenol A comprising the steps of: (a) providing a molten Bisphenol A compound; (b) adding a sufficient amount of base catalyst to the molten Bisphenol A compound to form a catalyst-containing mixture; (c) heating and pressurizing the catalyst-containing mixture; (d) adding a first amount of at least one alkylene oxide compound to the catalyst-containing mixture; (e) allowing the mixture of step "d" to equilibrate for a period of about 1 hour to about 6 hours; (f) adding a second amount of the at least one alkylene oxide compound to the mixture of step "e;" (g) allowing the mixture of step "f" to further react; and (h) allowing the mixture to cool and provide an alkoxylated Bisphenol A composition comprising residual Bisphenol A in an amount that is greater than zero but less than 200 ppm.

In another aspect, this invention relates to a method for preparing an alkoxylated Bisphenol A composition containing low residual Bisphenol A comprising the sequential steps of: (a) reacting Bisphenol A with a first amount of alkylene oxide in the presence of at least one alkaline catalyst at elevated temperature and pressure to form a mixture; (b) allowing the reaction to equilibrate for a period of time from about 1 hour to about 6 hours; (c) reacting the mixture of step "a" with a second amount of alkylene oxide in the presence of at least one alkaline catalyst at elevated temperature and pressure; and (d) allowing the mixture to cool and form an alkoxylated Bisphenol A composition comprising residual Bisphenol A in an amount greater than zero and less than 200 ppm.

DETAILED DESCRIPTION OF THE INVENTION

Definitions

In one aspect, Bisphenol A is the product of the reaction of phenol with acetone, wherein the molar ratio of phenol to acetone is about 2:1.

As used herein, the articles including "the", "a" and "an" when used in a claim, are understood to mean one or more of what is claimed or described.

As used herein, the terms "include", "includes" and "including" are meant to be non-limiting.

As a consequence of their manufacturing process, the Bisphenol A alkoxylated materials having low Bisphenol A content disclosed herein may contain a distribution of Bisphenol A oligomers.

More specifically, the Bisphenol A alkoxylated materials having low Bisphenol A content disclosed herein may contain a Poisson Distribution of Bisphenol A oligomers.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

Alkoxylated Bisphenol A

This invention encompasses an alkoxylated Bisphenol A composition represented by general structure (I):

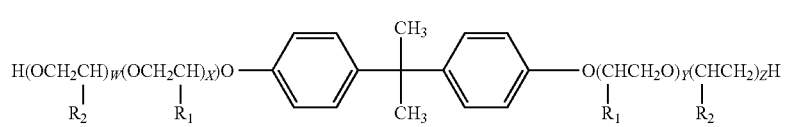

wherein $R_1$ and $R_2$ are independently selected from H, $CH_3$, $CH_2CH_3$ and wherein x+y=2.2 to 50 and w+z=0 to 50.

In one aspect, the term "residual Bisphenol A" is intended to include amounts of Bisphenol A greater than zero but less than 200 ppm, or greater than zero but less than 100 ppm, or greater than zero but less than 60 ppm. In one aspect, the term "residual" is intended to mean "unreacted." In yet another aspect, the term "residual Bisphenol A" is intended to include amounts of Bisphenol A in the range from 1 to 200 ppm, or in the range from 1 to 100 ppm, or in the range from 1 to 60 ppm.

In yet another aspect, the term "residual Bisphenol A" is intended to include amounts of Bisphenol A greater than zero but less than 5% by weight of the total composition, or greater than zero but less than 3% by weight of the total composition, greater than zero but less than 1% by weight of the total composition, or greater than zero but less than 0.5% by weight of the total composition. In yet another aspect, the term "residual Bisphenol A" is intended to include amounts of Bisphenol A in the range from 0.0001% to 5% by weight of the total composition, or in the range from 0.0001% to 3% by weight of the total composition, or in the range from 0.0001% to 1% by weight of the total composition, or in the range from 0.0001% to 0.5% by weight of the total composition.

Bisphenol A compounds are generally known to those skilled in the art. They include, for example, those Bisphenol A compounds disclosed in U.S. Pat. No. 6,858,759 to Oyevaar et al.; U.S. Pat. No. 7,696,388 to Belfadhel et al.; and U.S. Pat. No. 8,044,248 to Palmer; as well as those commercially available from Milliken & Company under the trade name Syn Fac.

The Bisphenol A compound is represented by general structure (II):

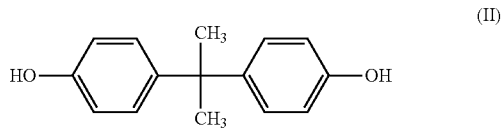 [SMILES: CC(C)(c1ccc(O)cc1)c1ccc(O)cc1]

Typical alkylene oxides which may be employed to alkoxylate the Bisphenol A compound include alkylene oxide monomers containing from two to twenty carbon atoms, or more preferably, from two to six carbon atoms. Examples of suitable alkylene oxide include Ethylene Oxide; Propylene Oxide; Butylene Oxide; oxetane; tetrahydrafuran; and mixtures thereof. The ratio of at least one alkylene oxide compound and a Bisphenol A compound may be in the range from about 50 to 1 and about 2 to 1.

Method for Preparing Alkoxylated Bisphenol A

Bisphenol A alkoxylates are prepared by means of the base-catalyzed addition of at least one alkylene oxide compound to a Bisphenol A compound at elevated temperature and pressure. In one aspect, the Bisphenol A compound may be in a molten state. In general, a reactor is charged with solvent, Bisphenol A and a catalyst. Water is stripped from the reactor, and then the alkylene oxide compound is added to achieve the desired level of ethoxylation.

For example, Bisphenol A ethoxylates are prepared by means of the base-catalyzed addition of an Ethylene Oxide to Bisphenol A at elevated temperature and pressure. A typical reaction scheme may generally be carried out as shown below:

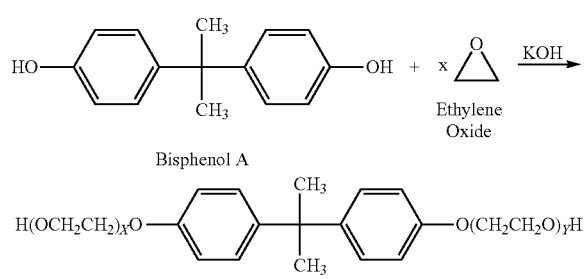

Typically, the addition of alkylene oxide (e.g. Ethylene Oxide) to the Bisphenol A is carried out as rapidly as possible until all the alkylene oxide has been added. By carrying out the addition process quickly, the speed with which alkoxylated Bisphenol A can be made is greater and production amounts and/or rates are higher.

The degree of polymerization of the resulting alkoxylated Bisphenol A is determined by the total amount of alkylene oxide added and by the combination of x+y in the reaction scheme. The degree of polymerization may be any integer, and/or fraction of an integer, greater than 2. In one aspect, x+y is between 2.2 and 50. When alkylene oxide is added by prior art methods, there remains a significant amount (greater than 200 ppm) of residual Bisphenol A in the alkoxylated Bisphenol A product. This has been found to be true even in products where x+y equals 20 or more. As discussed previously, this amount of residual Bisphenol A is not desired in many end-use products such as direct and indirect food contact packaging materials.

In general, any alkaline catalyst and/or alkaline metal catalyst may be utilized in the present alkoxylation reaction process. For example, and without limitation, base catalysts that may be suitable for use in the alkoxylation reaction process include potassium hydroxide, sodium hydroxide, calcium hydroxide, barium hydroxide, lithium hydroxide, and the like, and mixtures thereof. Typically, small amounts of the alkaline catalyst are needed. In one aspect, the amount of alkaline catalyst included in the alkoxylation reaction process is in the range from about 0.001% to 5% by weight, or in the range from about 0.01% to about 3% by weight, or in the range from about 0.1% to about 1% by weight.

Temperatures and pressures in the reaction process are somewhat dependent upon the equipment that is utilized for the manufacturing process. In general, any combination of temperature and pressure may be used that allows for the reaction to be carried out in an efficient and economical manner and that results in an alkoxylated Bisphenol A composition having less than 200 ppm of residual Bisphenol A present. Thus, in one aspect, processing temperatures may be in the range from about 90° C. to about 200° C., or in the range from about 115° C. to about 175° C., or in the range from about 125° C. to about 165° C. Pressures may be in the range from about 5 psi to about 160 psi, or in the range from about 5 psi to about 100 psi, or in the range from about 5 psi to about 70 psi.

The amount of time between the first addition of alkylene oxide and the second addition of alkylene oxide (or the amount of time the reaction is halted and allowed to rest after the first addition of alkylene oxide) is in the range of from about 1 hour and about 6 hours, or in the range from about 2 hours and about 5 hours, or in the range from about 2.5 hours and about 3.5 hours. In one aspect, the amount of time the reaction is stopped after addition of the first amount of alkylene oxide is about 3 hours.

Thus, an extended period of time exists between the first addition of alkylene oxide to the Bisphenol A compound (which reacts to form alkoxylated Bisphenol A) and the second addition of alkylene oxide. Accordingly, a rest period, wherein the process is stopped and the material is held at elevated temperature and pressure, is inserted into the manufacturing process. As a result, the method for preparing the composition of the present invention may be characterized as a non-continuous process. By increasing the length of time it takes to manufacture the alkoxylated Bisphenol A compound (by inserting this "rest period"), the amount of residual Bisphenol A remaining in the final product is reduced and such a reduction is achieved on a consistent basis. This discovery is considered to be unexpected and counter-intuitive to normal manufacturing processes.

Solvents may be used in the alkylation reaction process of the present invention. In one aspect, non-protic solvents may be useful. The solvent utilized in the alkoxylation reaction process may be one that is non-reactive with the alkylene oxide material. For example, suitable solvents that may be utilized include, without limitation, organic solvents such as toluene, ketones, and the like, and mixtures thereof.

Thus, the present invention is directed to a low residual Bisphenol A alkoxylated material and the process for making such material. In one aspect, it has been discovered that halting the alkylene oxide addition process step after approximately 2 moles of alkylene oxide has been added and allowing the reaction mixture to equilibrate for a short period of time before alkylene oxide addition is resumed, then the resulting alkoxylated Bisphenol A product contains significantly lower residual Bisphenol A.

Additional processing steps may be optionally employed to further neutralize and/or filter the resulting alkoxylated Bisphenol A product. Several of these optional steps are disclosed, for example, in U.S. Pat. No. 6,342,641 to VanDahm et al., which is entirely incorporated by reference herein.

Applications for Alkoxylated Bisphenol A

The alkoxylated Bisphenol A of the present invention may be useful for end-use applications such as, and without limitation, direct and/or indirect food packaging materials, container linings, printing inks and any other application wherein it is desirable to incorporate a processing additive as described herein.

EXAMPLES

Having generally described the invention, a further understanding can be obtained by reference to certain specific examples which are provided herein for purposes of illustration only and are not intended to be limiting unless otherwise specified.

Each of the Examples was prepared using standard reactor equipment and was carried out under elevated temperature and pressure. The amount of residual Bisphenol A was determined by means of gas chromatography using an Agilent Model 6890 Gas Chromatograph equipped with a 15 meter DB-5 capillary column and a Flame Ionization Detector. Amounts were quantified by comparison to external Bisphenol A standards.

Example 1

2593 grams of a four mole ethoxylate of Bisphenol A was prepared through reaction of 1374 grams of molten Bisphenol A with a first amount of 575 grams (2.2 moles) of Ethylene Oxide in the presence of 4 grams of Potassium Hydroxide at 130° C. and a post reaction time of 3 hours. The resultant amount of unreacted Bisphenol A was 440 ppm. 640 grams (1.8 moles) of a second additional amount of Ethylene Oxide was reacted at 130° C. and a post reaction of 1 hour. The resultant amount of unreacted Bisphenol A was 33 ppm.

Example 2

2593 grams of a four mole ethoxylate of Bisphenol A was prepared through reaction of 1374 grams of molten Bisphenol A with a first amount of 575 grams (2.2 moles) of Ethylene Oxide in the presence of 4 grams of Potassium Hydroxide at 130° C. and a post reaction time of 3 hours. The resultant amount of unreacted Bisphenol A was 480 ppm. 640 grams (1.8 moles) of a second additional amount of Ethylene Oxide was reacted at 130° C. and a post reaction of 1 hour. The resultant amount of unreacted Bisphenol A was 44 ppm.

Example 3

2505 grams of a three mole ethoxylate of Bisphenol A was prepared through reaction of 1541 grams of molten Bisphenol A with a first amount of 645 grams (2.2 moles) of Ethylene Oxide in the presence of 4 grams of Potassium Hydroxide at 130° C. and a post reaction time of 3 hours. The resultant amount of unreacted Bisphenol A was 841 ppm. 315 grams (0.8 mole) of a second additional amount of Ethylene Oxide was reacted at 130° C. and a post reaction of 1 hour. The resultant amount of unreacted Bisphenol A was 36 ppm.

Example 4

2353 grams of a three mole ethoxylate of Bisphenol A was prepared through reaction of 1449 grams of molten Bisphenol A with a first amount of 605 grams (2.2 moles) of Ethylene Oxide in the presence of 3.75 grams of Potassium Hydroxide at 130° C. and a post reaction time of 3 hours. The resultant amount of unreacted Bisphenol A was 850 ppm. 295 grams (0.8 mole) of a second additional amount of Ethylene Oxide was reacted at 130° C. and a post reaction of 1 hour. The resultant amount of unreacted Bisphenol A was 40 ppm.

Example 5

Comparative 1902 grams of a three mole ethoxylate of Bisphenol A was prepared through reaction of 1200 grams of molten Bisphenol A with 695 grams of Ethylene Oxide in the presence of 7 grams of Potassium Hydroxide at 130° C. and a post reaction time of 1 hour. The resultant amount of unreacted Bisphenol A was 137 ppm.

Example 6

Comparative 1902 grams of a three mole ethoxylate of Bisphenol A was prepared through reaction of 1200 grams of molten Bisphenol A with 695 grams of Ethylene Oxide in the presence of 7 grams of Potassium Hydroxide at 130° C. and a post reaction time of 1 hour. The resultant amount of unreacted Bisphenol A was 520 ppm.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited herein are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A method for preparing an alkoxylated Bisphenol A composition containing low residual Bisphenol A comprising the steps of:
   (a) providing a molten Bisphenol A compound;
   (b) adding a sufficient amount of base catalyst to the molten Bisphenol A compound to form a catalyst-containing mixture;
   (c) heating and pressurizing the catalyst-containing mixture;
   (d) adding a first amount of at least one alkylene oxide compound to the catalyst-containing mixture;
   (e) allowing the mixture of step "d" to equilibrate for a period of about 1 hour to about 6 hours;
   (f) adding a second amount of the at least one alkylene oxide compound to the mixture of step "e;"
   (g) allowing the mixture of step "f" to further react; and
   (h) allowing the mixture to cool and provide an alkoxylated Bisphenol A composition comprising residual Bisphenol A in an amount that is greater than zero but less than 200 ppm.

2. The method of claim 1, wherein the ratio of the at least one alkylene oxide compound and the molten Bisphenol A compound is in the range from about 50 to 1 and about 2 to 1.

3. The method of claim 1, wherein the at least one alkylene oxide compound is selected from the group consisting of Ethylene Oxide; Propylene Oxide; Butylene Oxide; oxetane; tetrahydrafuran; and mixtures thereof.

4. The method of claim 3, wherein the at least one alkylene oxide compound is Ethylene Oxide.

5. The method of claim 1, wherein the step of heating and pressurizing the catalyst-containing mixture occurs at a temperature of between about 90° C. and about 200° C. and a pressure of between about 5 psi and about 160 psi.

6. A method for preparing an alkoxylated Bisphenol A composition containing low residual Bisphenol A comprising the sequential steps of:
   (a) reacting Bisphenol A with a first amount of alkylene oxide in the presence of at least one alkaline catalyst at elevated temperature and pressure to form a mixture;
   (b) allowing the reaction to equilibrate for a period of time from about 1 hour to about 6 hours;
   (c) reacting the mixture of step "a" with a second amount of alkylene oxide in the presence of at least one alkaline catalyst at elevated temperature and pressure; and (d) allowing the mixture to cool and form an alkoxylated Bisphenol A composition comprising residual Bisphenol A in an amount greater than zero and less than 200 ppm.

* * * * *